(12) United States Patent
Rusin et al.

(10) Patent No.: US 10,485,486 B2
(45) Date of Patent: Nov. 26, 2019

(54) CLINICAL METRIC FOR PREDICTING ONSET OF CARDIORESPIRATORY DETERIORATION IN PATIENTS

(71) Applicant: Baylor College of Medicine, Houston, TX (US)

(72) Inventors: Craig Rusin, Houston, TX (US); Kenneth M. Brady, Houston, TX (US); Eric Vu, Houston, TX (US); Sebastian Acosta, Houston, TX (US); Daniel J. Penny, Houston, TX (US)

(73) Assignee: Baylor College of Medicine, Houston, TX (US)

( * ) Notice: Subject to any disclaimer, the term of this patent is extended or adjusted under 35 U.S.C. 154(b) by 509 days.

(21) Appl. No.: 14/942,722

(22) Filed: Nov. 16, 2015

(65) Prior Publication Data
US 2016/0135756 A1   May 19, 2016

Related U.S. Application Data

(60) Provisional application No. 62/081,446, filed on Nov. 18, 2014.

(51) Int. Cl.
| | |
|---|---|
| *A61B 5/00* | (2006.01) |
| *A61B 5/0205* | (2006.01) |
| *A61B 5/021* | (2006.01) |
| *A61B 5/024* | (2006.01) |
| *A61B 5/0402* | (2006.01) |
| *A61B 5/1455* | (2006.01) |
| *A61B 5/08* | (2006.01) |

(52) U.S. Cl.
CPC ........ *A61B 5/7275* (2013.01); *A61B 5/02055* (2013.01); *A61B 5/7282* (2013.01); *A61B 5/021* (2013.01); *A61B 5/02405* (2013.01); *A61B 5/0402* (2013.01); *A61B 5/0816* (2013.01); *A61B 5/14551* (2013.01); *A61B 5/7246* (2013.01); *A61B 5/746* (2013.01)

(58) Field of Classification Search
USPC ................................................. 600/300–301
See application file for complete search history.

(56) References Cited

U.S. PATENT DOCUMENTS

| | | | | |
|---|---|---|---|---|
| 7,435,221 | B1* | 10/2008 | Bharmi | A61B 5/02405 600/484 |
| 2007/0118054 | A1* | 5/2007 | Pinhas | A61B 5/1102 600/587 |
| 2008/0214904 | A1* | 9/2008 | Saeed | A61B 5/0006 600/301 |
| 2016/0143594 | A1* | 5/2016 | Moorman | A61B 5/02405 705/2 |

* cited by examiner

*Primary Examiner* — Nicole F Lavert
(74) *Attorney, Agent, or Firm* — Schafer IP Law

(57) ABSTRACT

A system generates and displays a clinical metric based on continuously collected patient physiological data, wherein the clinical metric provides a predictive measure of the likelihood of the onset of a cardiorespiratory deterioration event in the patient in a predetermined time period in the future. If the clinical metric has a configured relationship with a predetermined threshold value, embodiments may generate an alarm in addition to or instead of displaying the clinical metric. The clinical metric thus allows clinical staff to take medically indicated actions to prevent or reduce the effects of the predicted deterioration.

20 Claims, 11 Drawing Sheets

CLINICAL METRIC FOR PREDICTING ONSET OF CARDIORESPIRATORY DETERIORATION IN PATIENTS

TECHNICAL FIELD

The present invention relates to the field of clinical care, and in particular to techniques for predicting an onset of cardiorespiratory deterioration in a patient based upon information from physiological sensors.

BACKGROUND ART

Current methods of predicting the onset of cardiorespiratory deterioration have numerous limitations in terms of accuracy, speed, and efficiency. Various embodiments of the present disclosure address these limitations.

BRIEF DESCRIPTION OF DRAWINGS

The accompanying drawings, which are incorporated in and constitute a part of this specification, illustrate an implementation of apparatus and methods consistent with the present invention and, together with the detailed description, serve to explain advantages and principles consistent with the invention. In the drawings.

DESCRIPTION OF EMBODIMENTS

Figure 1:
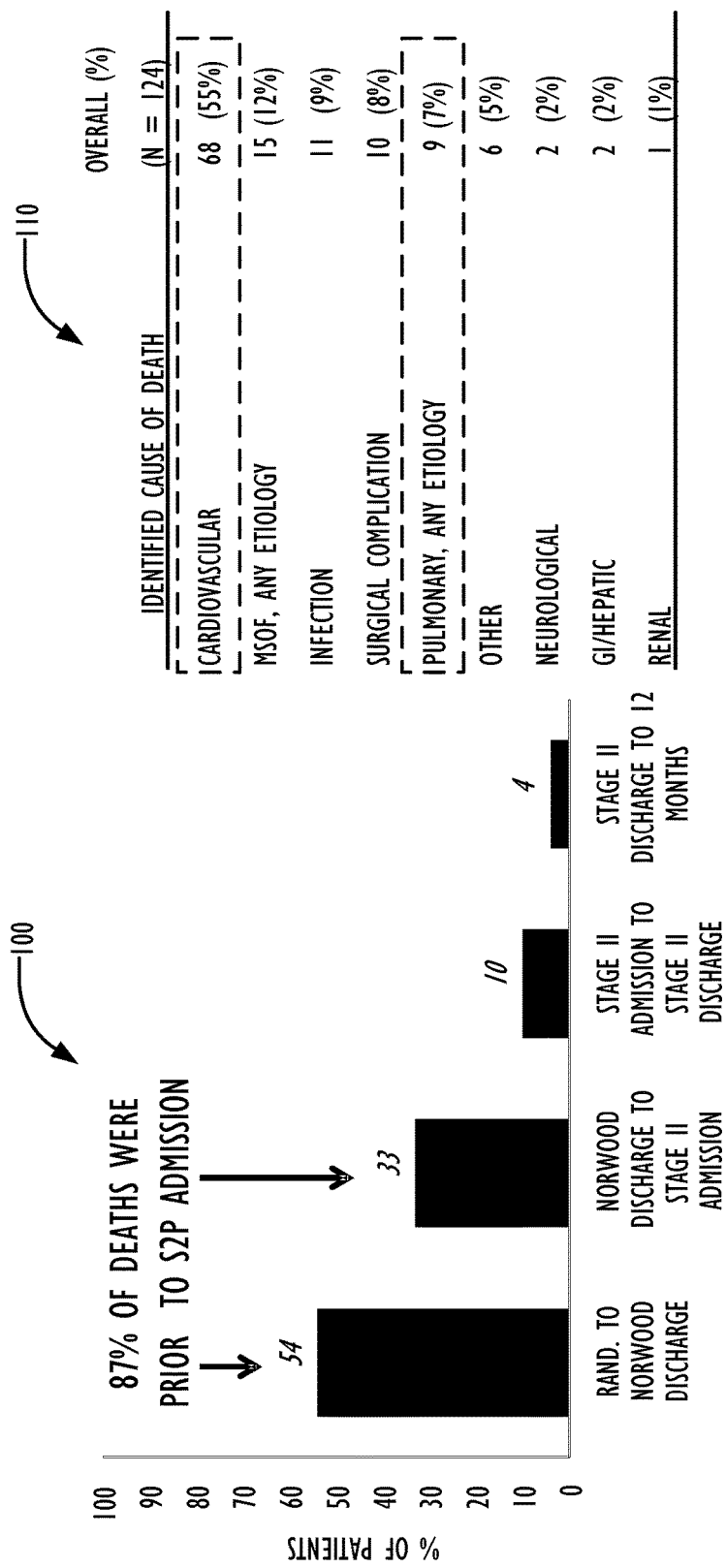
FIG. 1 is a graph and table illustrating cause and timing of death of single ventricle patients according to the prior art.

In the following description, for purposes of explanation, numerous specific details are set forth in order to provide a thorough understanding of the invention. It will be apparent, however, to one skilled in the art that the invention may be practiced without these specific details. In other instances, structure and devices are shown in block diagram form in order to avoid obscuring the invention. References to numbers without subscripts are understood to reference all instance of subscripts corresponding to the referenced number. Moreover, the language used in this disclosure has been principally selected for readability and instructional purposes, and may not have been selected to delineate or circumscribe the inventive subject matter, resort to the claims being necessary to determine such inventive subject matter. Reference in the specification to "one embodiment" or to "an embodiment" means that a particular feature, structure, or characteristic described in connection with the embodiments is included in at least one embodiment of the invention, and multiple references to "one embodiment" or "an embodiment" should not be understood as necessarily all referring to the same embodiment.

Although some of the following description is written in terms that relate to software or firmware, embodiments can implement the features and functionality described herein in software, firmware, or hardware as desired, including any combination of software, firmware, and hardware. References to daemons, drivers, engines, modules, or routines should not be considered as suggesting a limitation of the embodiment to any type of implementation.

The section headings used herein are for organizational purposes and are not to be construed as limiting the subject matter described. All documents, or portions of documents, cited in this application, including, but not limited to, patents, patent applications, articles, books, and treatises, are hereby expressly incorporated herein by reference in their entirety for any purpose. In the event that one or more of the incorporated literature and similar materials defines a term in a manner that contradicts the definition of that term in this application, this application controls.

As used herein, "real time" means reporting, depicting, or reacting to events at the same rate and at the same time as they occur, without significant delay. Similarly, "near real time" pertains to the timeliness of data or information that has been delayed by the time required for electronic communication and automatic data processing. This implies that there are no significant delays. For clarity, as used herein, "real time" is to be read as incorporating "near real time."

As used herein, the term "medium" encompasses a collection of media that together hold the contents described as being held by the medium.

As used herein, the term "a computer" or "a computer system" can refer to a single computer or a plurality of computers working together to perform the function described as being performed on or by a computer system.

Although the description below is written in terms of predicting cardiorespiratory deterioration of patients after stage 1 palliation (S1P) for hypoplastic left heart syndrome (HLHS) and related lesions, the techniques described below may be used for other patient classes and syndromes, and are not limited to HLHS patients.

The management of newborns after surgical palliation for congenital heart disease is complex and challenging. Infants with a single functional ventricle are at highest risk of sudden death before establishment of a serial pulmonary circulation with staged palliative surgeries. The most well-known single ventricle lesion is HLHS, which, while accounting for only 2-3% of all congenital heart disease, is responsible for up to 25-40% of all neonatal cardiac deaths. As illustrated in graph 100 of FIG. 1, a Single Ventricle Reconstruction trial demonstrated that for subjects undergoing palliation for HLHS, 87% of deaths occurred prior to the stage 2 palliative surgery, when the parallel circulation is replaced with a cavo-pulmonary shunt, with more than 30% of these deaths occurring during the inter-stage period, after the Norwood (Stage 1) discharge to admission to Stage 2. As illustrated in table 110 of FIG. 1, of those deaths with identifiable causes, 62% were related to either cardiovascular or pulmonary deterioration.

Thus, patients after S1P for HLHS and related lesions are still at risk of life threatening cardiorespiratory deterioration resulting in shock, cardiac arrest, and hypoxemia. These cardiorespiratory deteriorations may be forecast by subtle, previously unidentified changes in cardiorespiratory dynamics. Identification of these precursors may provide an opportunity for early, life-saving intervention.

Figure 2:
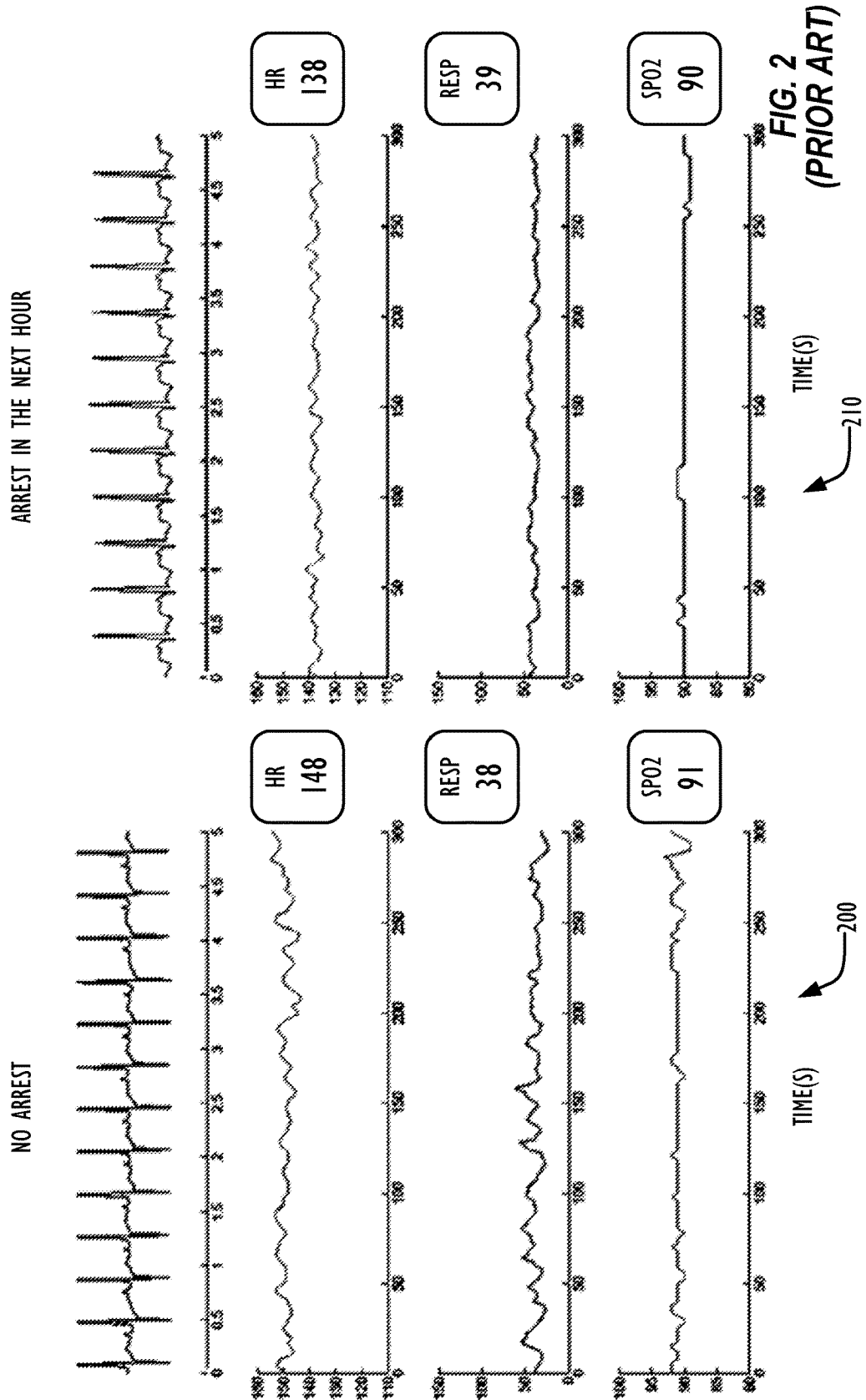
FIG. 2 is a collection of graphs showing vital signs for a patient who did not arrest and a patient who did arrest, according to the prior art.

Infants who require surgical palliation of congenital heart disease are monitored intensely and continuously. The reason for this is simple: the sooner the care team can detect that a patient is deteriorating, the quicker they can intervene to prevent catastrophic events from occurring. Vigilant monitoring improves survival of single ventricle patients. Home monitoring following hospital discharge from stage 1 palliation has been associated with improved survival. While these children are intensely monitored, standard monitoring techniques have not been optimized for forecasting the onset of deterioration. As a result, sub-clinical precursors hidden within the physiological data which precedes these events cannot be easily identified at the bedside. For example, FIG. 2 illustrates the physiological data collected from 2 HLHS patients: The patient whose vital signs are illustrated in graph 200 arrested one hour after this data was obtained, while the patient whose vital signs are illustrated in graph 210 did not.

Detecting impending deterioration from vital signs data such as traditionally displayed in graphs 200 and 210 can be difficult, even for experienced physicians, because current monitoring technologies are not optimized for such infants. For example, in the cardiac intensive care unit, patient monitoring may be confounded by baseline abnormalities of standard vital signs such as pulse-oximetry ($SpO_2$), arterial blood pressure (ABP), and electrocardiogram (ECG). Thus, even when flow to the parallel pulmonary and systemic circulations are optimally balanced, patients may be cyanotic. Pulmonary runoff from a systemic to pulmonary shunt can cause low diastolic arterial blood pressure. Cardiac conduction abnormalities can cause the ST segments to be elevated or depressed, so routine ECG monitoring may not be useful to discriminate the status of myocardial perfusion. What is needed is a patient monitoring system that is specifically optimized to detect problems in the unique physiology of patients with parallel systemic and pulmonary circulation, rather than for the general patient population.

Figure 3:
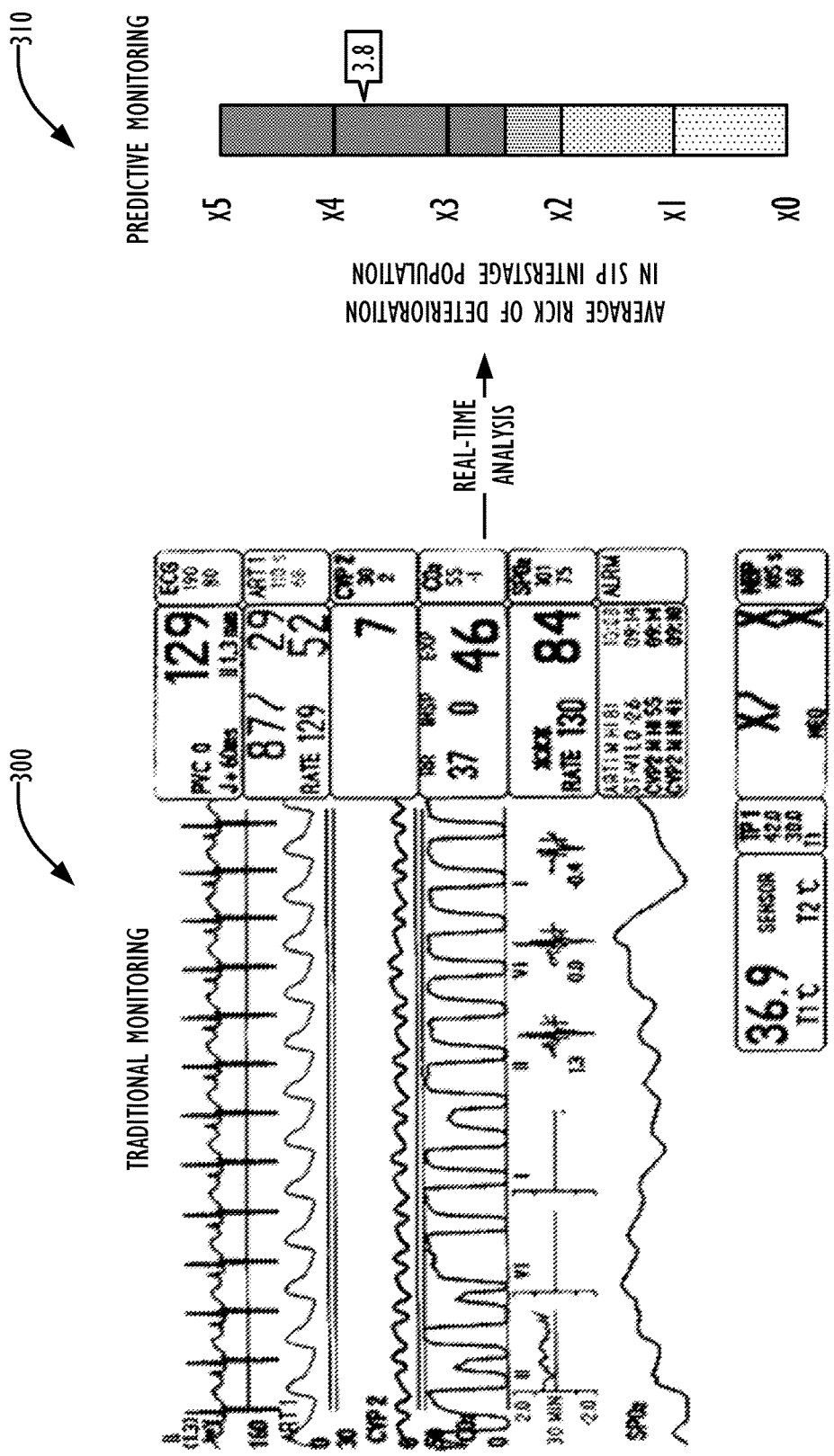
FIG. 3 is a block diagram comparing traditional vital sign monitoring and predictive monitoring according to one embodiment.

A new metric (a risk index) is described below, which is derived from continuous physiologic measurements from, and predictive of imminent deterioration for subjects with parallel systemic and pulmonary circulations, prior to stage 2 palliation. FIG. 3 is a pair of graphs illustrating the value of such a metric. Similar to the graphs of FIG. 2, graph 300 displays a traditional vital signs display of physiological data collected from physiological sensors attached to the patient. Graph 310 illustrates a simple predictive metric that can be used to predict the risk the onset of cardiorespiratory deterioration in the patient, expressed as a risk multiplier. While the techniques used to generate the clinical metric are similar to those used in a traditional observational study, multivariate regression analysis of factors related to deterioration, the process of predictive model development is fundamentally different. Rather than test for physiologic differences between subjects that experience a deterioration and those that do not, the approached used herein asserts that physiology immediately prior to deterioration is abnormal, and that physiology not recorded in close proximity to deterioration events is stable. From this assertion, a classification model is constructed to maximize the recognition of pre-deterioration physiology from stable physiology based on recorded data. Therefore, the clinical metric, sometimes referred to as a risk index, is a measure of how similar a patient's current physiology is to physiology which occurs just prior to a critical deterioration event (CDE). Real time utilization of this index may provide the opportunity for clinicians to perform early interventions before deterioration becomes life-threatening, potentially impacting patient morbidity and mortality.

A one year prospective observational study was conducted of infants who underwent surgical palliation at Texas Children's Hospital (TCH) in Houston, Tex. Approval was obtained from the Institutional Review Board (IRB) at the Baylor College of Medicine (BCM) with a waiver of consent prior to the start of the study. Eligible subjects had any anatomic diagnosis of either a morphologic left or right ventricle, provided their early neonatal palliative surgery resulted in a mixing lesion with ventricular outflow to both pulmonary and systemic circulations. Subjects were enrolled upon admission to the cardiovascular intensive care unit immediately following early neonatal palliation, and enrollment continued until stage 2 palliation was performed (i.e. the interstage period). All 25 eligible subjects were enrolled and included in the analysis. Instances of critical deterioration were defined as the need for cardiopulmonary resuscitation (CPR) or endotracheal intubation, and were found via a chart review and verified using physiologic recordings from patients.

Patient Characteristics

Figure 4:
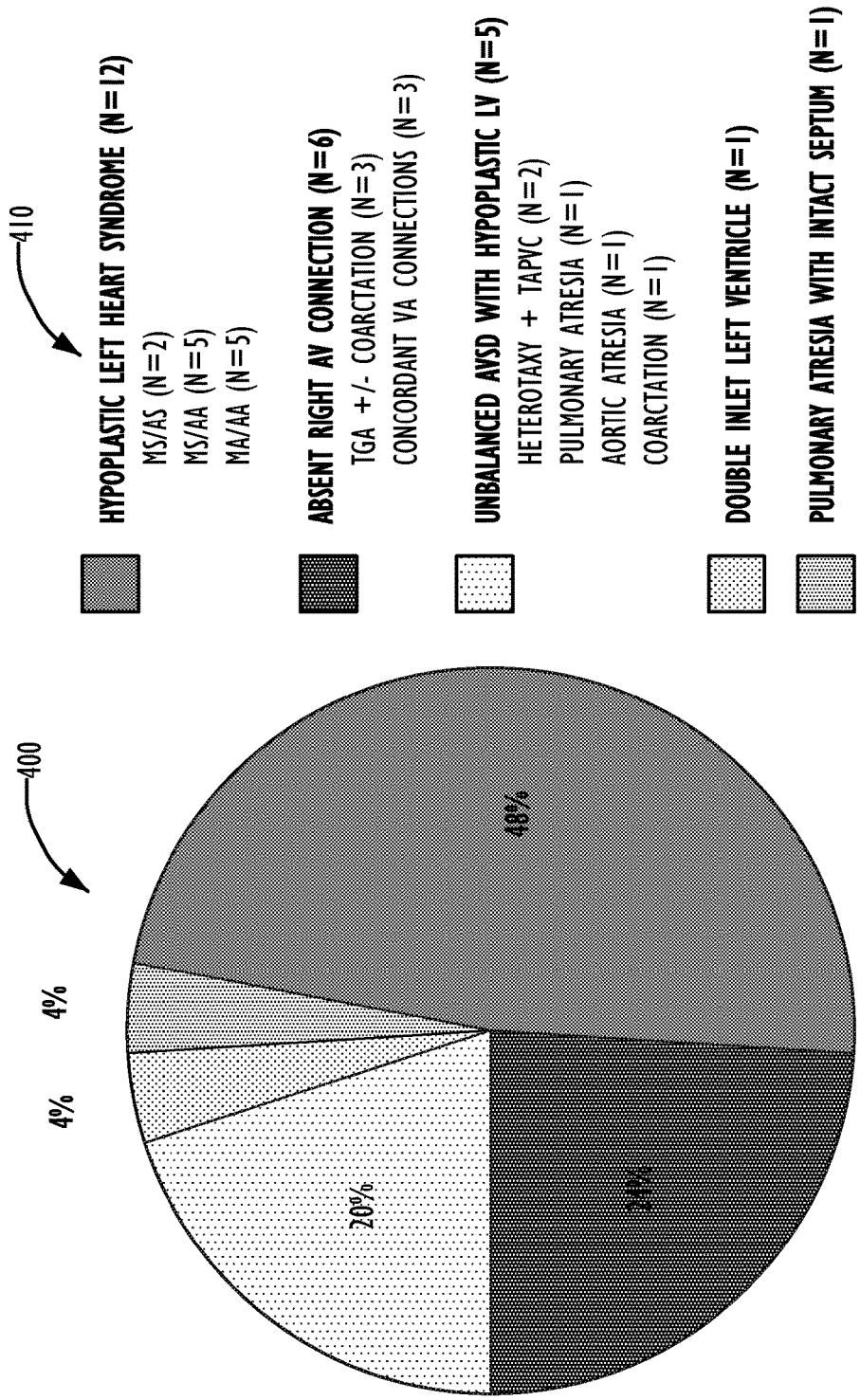
FIG. 4 is a pie chart illustrating a population of patients matching inclusion criteria used for generating a model for use in one embodiment.

FIG. 4 is a pie chart 400 illustrating the breakdown of the patients, with 48% of the patients having HLHS, 12 having an absent right atrioventricular connection, 5 having an unbalanced atrioventricular septal defect, one having a double inlet left ventricle, and 1 having pulmonary atresia with an intact septum. Twenty-five infants were included in this cohort. Their anatomical characteristics and surgical procedures are presented in the legend area 410. Of the 25 subjects, 13 had one or more cardiorespiratory deterioration events at some point during their interstage period (average 140±53 days), with a total of 20 observed events, occurring at a mean of 48±40 days after the initial surgery. Sixteen (73%) events were considered to be primarily respiratory in nature, while six (27%) were considered cardiac events. There were four hospital deaths in the cohort. The majority of the patients who were identified for the study remained hospitalized until their second stage of surgical palliation (bidirectional Glenn). As a result, we were able to capture complete high-resolution physiologic recordings for almost all of the patients in this cohort resulting in more than 72,000 hours of physiologic data.

A cluster-based supercomputing system was installed to collect and process all of the physiological data from all monitored patients at TCH in real time. The data was continuously recorded from 127 beds in the cardiovascular intensive care unit and the cardiology inpatient units using the using the Sickbay™ Platform (Medical Informatics Corp; Houston, Tex.) for the duration of the study, and collected 180 bed-years of data (about 10 TB of data) for 8,988 unique patients. Since the majority of the observed rapid response events occurred more than a month after the initial surgery, the model needed to be constructed using less invasive and more common forms of monitoring, but to be captured with the same high-resolution fidelity of the monitoring that are used in the operating room. We collected high frequency physiological waveforms from patient physiological sensors including electrocardiogram (ECG), arterial blood pressure (ABP), left atrial pressure (LAP), peripheral capillary oxygen saturation (SpO$_2$) and chest impedance (60 Hz-240 Hz), as well as heart rate (HR), respiration rate (RR), temperature, and ST segment vital signs (0.5 Hz) during the patient's interstage hospitalization. Signal conditioning was done prior to the analysis to reject noise and artifacts which are inherent in physiological data.

The data were stored on site for analysis, and automatically de-identified and coded by the Sickbay™ system to prevent the release of protected health information. Data analysis and model development was conducted using the Matlab™ programming environment (MATLAB is a registered trademark of The MathWorks; Natick, Mass.).

Figure 5:
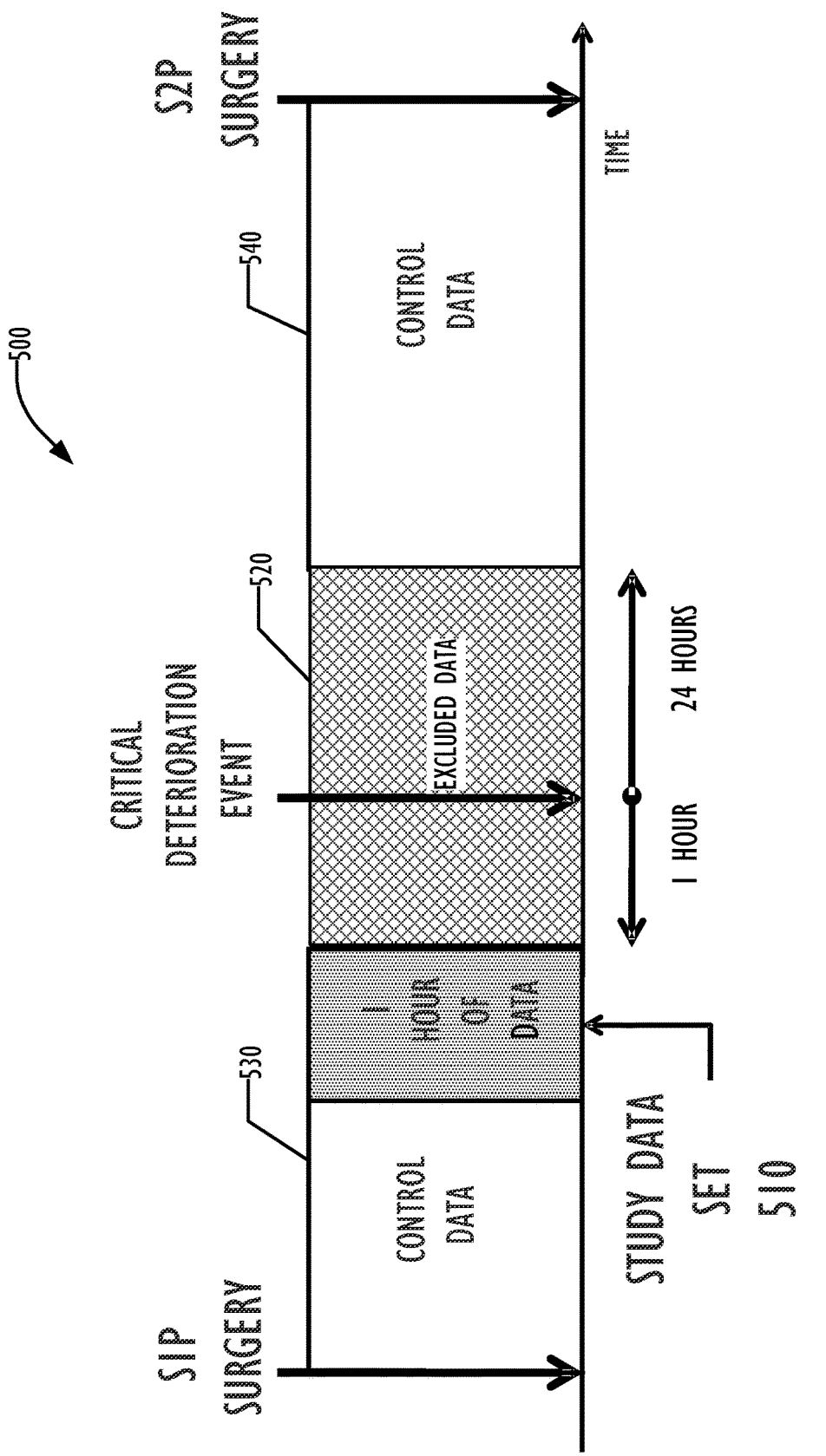
FIG. 5 is a graph illustrating groups of patient physiological data used to generate a a predictive model according to one embodiment.

As indicated in the graph 500 of FIG. 5, the physiological data collected from these patients was separated into a study group and a control group according to its proximity to a spontaneous rapid response event. Data that was collected 1-2 hours before an event was labeled as study data 510. Data collected less than 1 hour before an event and 24 hours after an event were excluded from the analysis. Rapid response events that occurred while the patient was on a ventilator were also excluded from the analysis. All of the remaining data between the two surgeries (early data 530 and later data 540) were labeled as control data.

To start the model development process, it was necessary to establish an objective criteria as to what constitutes a CDE, also known as a rapid response event. Signs of acute severe deterioration were identified and ranked by an expert team according to the RAND/UCLA method. as indicated below in Table 1. The need for CPR and the need for reintubation were ranked as more likely than not to be signs of acute deterioration. We defined these two events, taken together, as rapid response events.

TABLE 1

| Rank | Clinical Parameter | Likelihood Score |
| --- | --- | --- |
| 1 | Need for CPR | 9 |
| 2 | Epinephrine bolus | 9 |
| 3 | Phenylephrine bolus | 8.8 |
| 4 | Rise in Lactate of > 2 over up to 24 hours | 8.2 |
| 7 | Need for Reintubation | 7.7 |
| 5 | Thready pulses | 7.2 |
| 9 | Hypotension | 7.2 |
| 6 | Oxygen Extraction Ratio >50-60% | 7.1 |
| 8 | Poor capillary refill | 6.8 |
| 10 | Hypotension + Low SpO2 | 6.5 | where 9=more likely than not to be indicative of deterioration and 1=less likely than not to be indicative of deterioration.

25 patients matched inclusion criteria and 21 spontaneous CDEs were observed during the study period, as shown in Table 2 below:

TABLE 2

| | Total | # of Patients with Critical Deterioration Events | # of Patients w/o Critical Deterioration Events |
| --- | --- | --- | --- |
| Patients | 25 | 13 (52%) | 12 (48%) |
| Deaths | 4 | 4 (100%) | 0 (0%) |

Selecting Input Variables to the Algorithm

Candidate input variables to the algorithm were selected by a team of clinical experts based on physiologic rationale. This was done by delineating the etiologies of deterioration in these patients and then identifying measurable physiologic parameters which may be perturbed by these etiologies. Etiologies theorized to cause the observed events included cardiac ischemia, acute heart failure, shunt thrombosis, and changes in the systemic to pulmonary flow ratio due to changes in resistance of the respective vascular circuits. For each of these etiologies, a list of measurable candidate physiologic variables was generated. This comprehensive list was then reduced by practical limitations and by agreement between the experts. The total number of input variables were limited to 6 in order to minimize model over-fitting. The final list of inputs included variables directly sampled from the monitor and those that are derived from the primary monitored data: heart rate, SpO$_2$, respiration rate variability, beat-to-beat heart rate variability, ST segment from lead V1, and variability of the 3D ST segment vector.

A multivariate logistic regression classifier was selected as the basis for our predictive model. Several metrics were derived from the physiological data, including the variability of the ST segment vector as well as beat-to-beat Heart Rate Variability. These derived measures were joined with the patient vital signs and incorporated into the model optimization process. Although multivariate logistic regression techniques were used in the TCH study, other mathematical optimization techniques can be used to develop a predictive model in other embodiments.

Cardiac ischemia may be a prominent feature of the decompensation of infants with parallel circulation, but it is difficult to quantify with electrocardiogram monitoring because of conduction abnormalities which confound the predictive value of individual ST segment measurements. To overcome this limitation, we quantified the variability of the ST segment vector, which was constructed in three dimensions from the quasi-orthogonal leads V$_5$, II, and aVL. The x, y, and z coordinates of the instantaneous ST vector are given by equations (1)-(3):

$$ST_x = V_5 \sin(30°) \quad (1)$$

$$ST_y = aVL*\cos(30°) + II*\cos(60°) + V_5*\sin(30°) \quad (2)$$

$$ST_z = aVL*\sin(30°) - II*\sin(60°) \quad (3)$$

where V$_5$, II, and aVL are the values of the ST segments of the associated ECG leads. The movement of the ST vector was measured as the distance traveled by the tip of the vector over 30 second intervals. This interval was chosen to remove the rapid, non-physiologic changes in ST displacement generated by the monitors in use at TCH and because providers in the expert clinical panel reported the anecdotal occurrence of low-frequency changes in the ST segment, which are clinically viewed in 30 minute moving windows on the display screens used with the clinical monitors.

Classification Algorithm Construction

The physiologic data obtained from study subjects were separated into study (pre-deterioration) and control (non-deterioration) data sets. As stated above and illustrated in FIG. 5, the study data set included all physiologic data recorded in the time interval starting two hours prior to each deterioration event and ending one hour prior to the event. The control data set included all physiologic data recorded more than 2 hours before or 24 hours after a deterioration event. If a subject did not experience a deterioration event, then all of the patient's physiologic measurements were included in the control data set.

In one embodiment, data recorded between one hour prior to deterioration and 24 hours following a deterioration event are not included in the classification model. While this may be counterintuitive—physiology immediately preceding deterioration is most likely to be distinct from healthy physiology—there are two reasons to exclude these data. First, the acute decompensation state is not likely to be subtle, and is therefore likely to be recognized by the care providers, making event detection during this time window of limited clinical value. Second, the recognition of the pre-deterioration state by the care providers increases the likelihood of medical interventions that would distort the underlying physiology. Such interventions may potentially corrupt the model optimization process, creating an algorithm that recognizes the application of specific clinical interventions rather than physiologic precursors to critical deterioration. Similarly, deterioration events which occurred while the infant was mechanically ventilated were also not included in the model development process as the ventilator could potentially introduce non-physiologic characteristics into the study data set. These time periods are illustrative and by way of example only, and other time period for determining data to exclude may be used.

A multivariate logistic regression model of the form $$\ln\left(\frac{p}{1-p}\right) = \beta_0 + \sum_{j=1}^{J} \beta_j \frac{x_j - \mu_j}{\sigma_j} \quad (4)$$

was selected as the basis of the classification algorithm, where p is the probability that the input metrics $(x_1, x_2, \ldots, x_J)$ belong to the study data set, $\mu_j$ is the mean value of $x_j$ over the data set, and $\sigma_j$ is the standard deviation of $x_j$. The input metrics to the model were computed from the raw physiologic observations, $y_j(t)$. In one embodiment, baseline values were removed from the raw physiologic metrics prior to model optimization using equation (5) below:

$$x_j(t) = y_j(t) - y_j^{base}(t) \quad (5)$$

where $y_j^{base}(t)$ is the baseline value of metric j computed as the average of $y_j(t)$ over a window of time from six hours prior to time t. The regression coefficients, $\beta_j$, were found using least squares optimization, in order to maximize the ability of the algorithm to separate the study data set from the control data set. This produced an algorithm which was tuned to recognize only those physiologic patterns which occur 1-2 hours prior to the onset of cardiorespiratory deterioration. Other embodiments may omit the baseline elimination, or use a different baseline determination.

An index of the current risk of an rapid response event is formulated by normalizing the output of the predictive model with the mean probability of an event occurring in this population. We call this the relative risk index (RRI). A value of 1 represents the average risk of an event. A value of 2 indicates that the patient has twice the risk of an event as an average patient, while a value of 3 represents three times the average risk. Other risk indices calculated from the predictive model may be used as desired.

In one embodiment, the RRI is derived from the logistic regression model by normalizing the clinical metric to an average risk of deterioration for this population. A value of 1 represents that the infant is at average risk of having a critical deterioration event in the next few hours, while a value of 2 represents that the infant is at twice the average risk of deteriorating. The index can be continuously determined from the physiologic data of the patients collected from patient physiological sensors and can be used to provide a calibrated measure of risk of deterioration in the near future.

Characterization of Algorithm Performance

Figure 6:
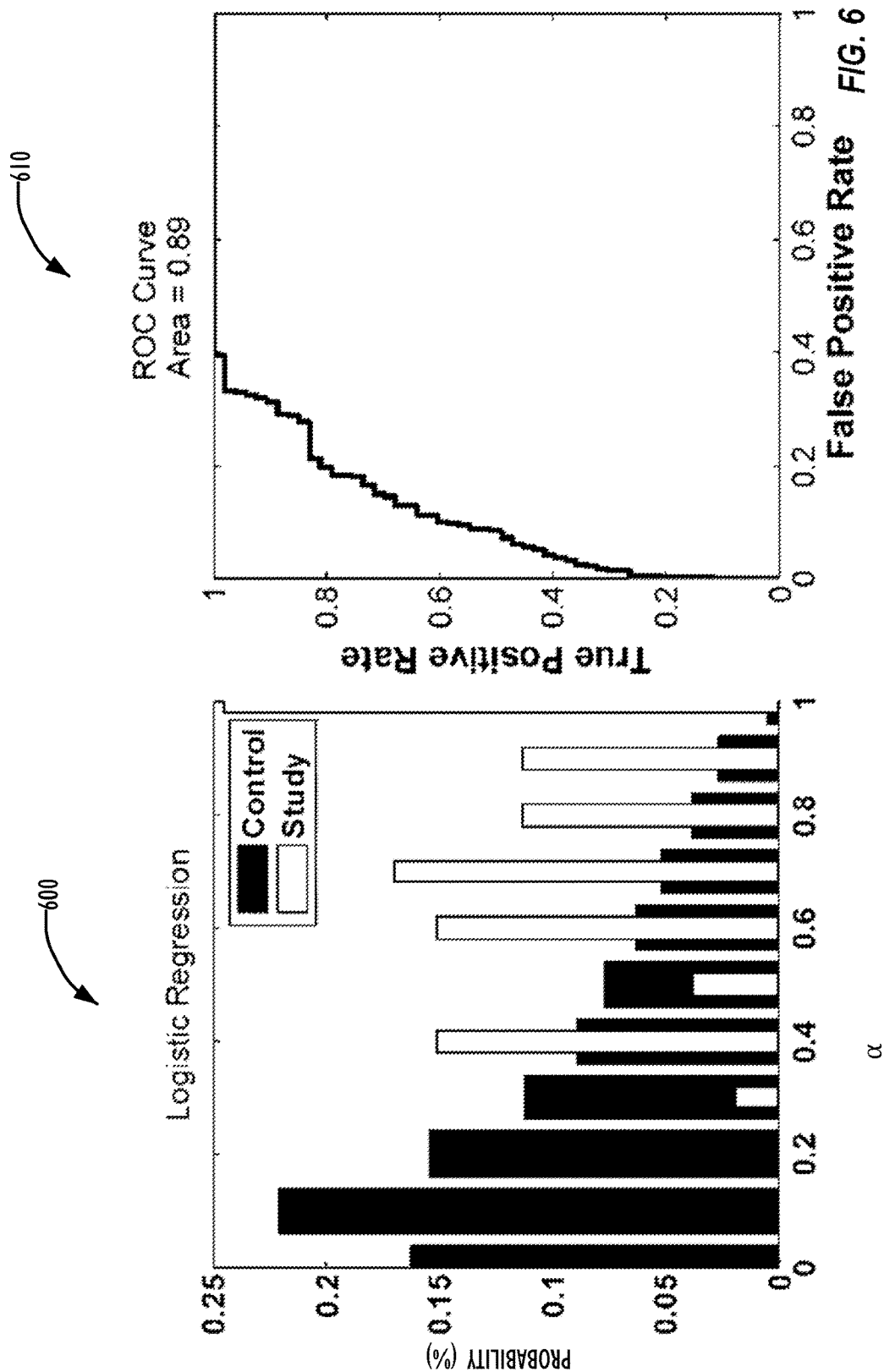
FIG. 6 are two graphs illustrating validation of a predictive model according to one embodiment.

The area under the Receiver Operating Characteristic (ROC) curve was used as the measure of the performance of the predictive model, as illustrated in graph 610 of FIG. 6. Ten-fold cross-validation was used to validate the predictive model, while numerical bootstrap aggregation was used to determine the statistical precision of the performance of the predictive algorithm. Bootstrapping was implemented using perfcurve function provided by Matlab, with 1,000 bootstrap replicas. This function returns the confidence bounds for the area under the ROC curve.

Predictive Performance of Algorithm

The coefficients of the algorithm were optimized to maximize the recognition of physiologic features most associated with the time period just prior to the critical deterioration event.

TABLE 3

| Input Parameter | p value |
| --- | --- |
| Heart Rate | <0.001 |
| Resp. Rate Variability | <0.001 |
| ST Segment (V1) | 0.045 |
| SpO$_2$ | <0.001 |
| N-N Heart Rate Variability | 0.052 |
| ST Segment Variability | 0.017 |

Elevated heart rate was found to have the largest coefficient, indicating that it has the largest contribution to recognizing precursors of cardiorespiratory deterioration. Other factors, in order of descending significance were: decreased respiration rate variability, decreased SpO$_2$, increased ST segment variability, ST segment depression, and decreased heart rate variability. The performance curves for the optimized model are shown in FIG. 6. Graph 600 is a histogram of the optimized classification algorithm for the control and pre-deterioration data sets projected on an axis of optimal separation a. Graph 610 illustrates a receiver operating characteristic curve for the optimized classification algorithm. In the examples of FIG. 6, which were calculated without baseline correction, the ROC area was calculated to be 0.89. In an embodiment employing baseline correction, the ROC area for the model was calculated to be 0.91 with a 95% confidence interval of 0.88-0.94, indicating good performance in separating characteristics associated with the pre-deterioration data from control measurements. Other optimized models may have different ROC areas. The sensitivity, specificity, and the positive likelihood ratio were calculated as a function of the choice of alerting threshold to determine the optimum operating threshold for utilizing the index. For a threshold of 3, in one embodiment the positive likelihood ratio is 10, while the sensitivity is 0.81 and the specificity is 0.84, while a threshold of 10, the positive likelihood ratio is 16, while the sensitivity is 0.40 and the specificity is 0.97. Other optimized models may have different likelihood ratios, sensitivities, and specificities.

Figure 7:
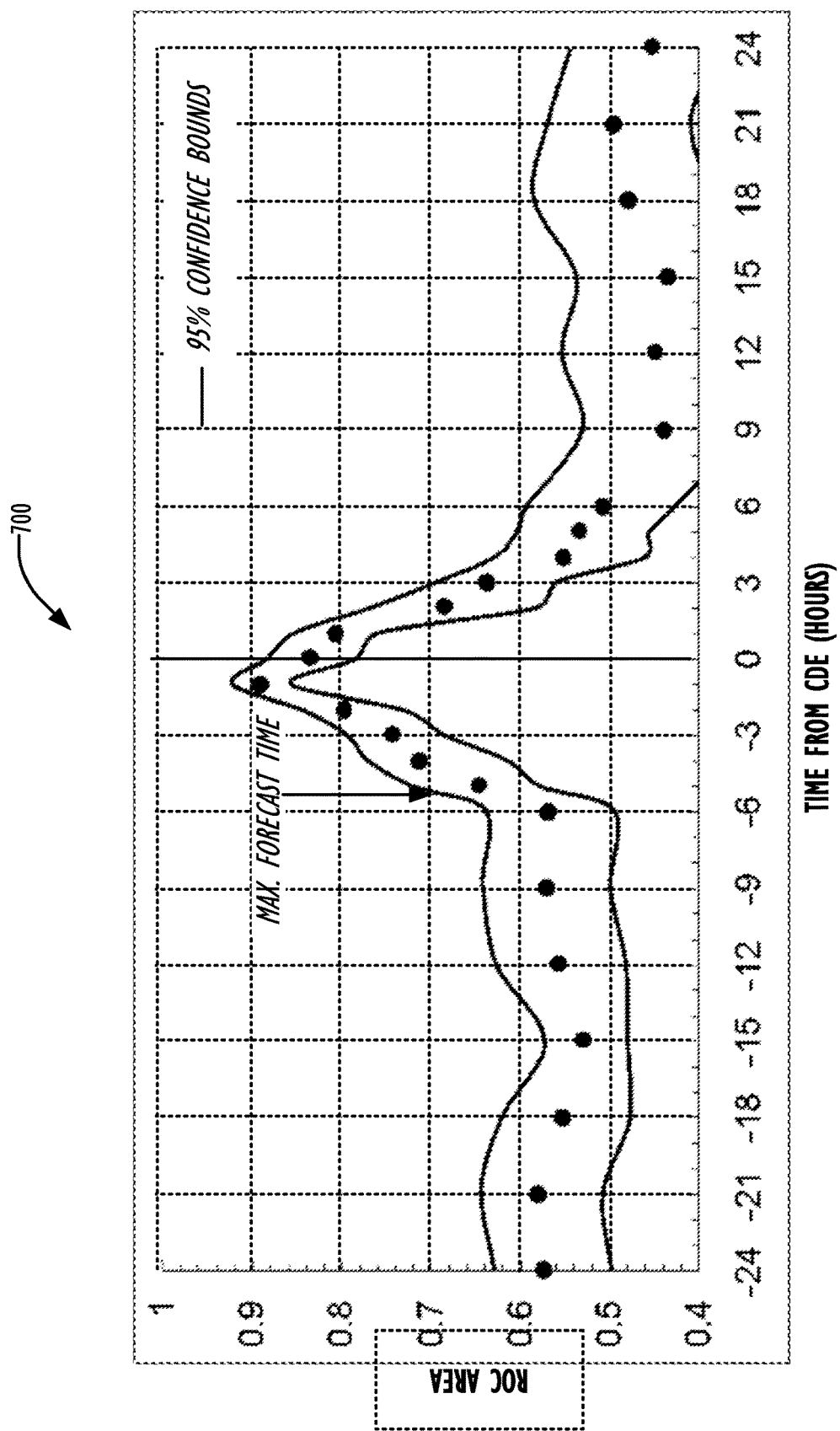
FIG. 7 is a graph illustrating the ability of a predictive model according to one embodiment at different time periods before and after a cardiorespiratory deterioration event.

In order to estimate how far in advance the algorithm could be used to detect an impending event, its performance was evaluated as a function of time from deterioration, as illustrated in graph 700 of FIG. 7. Each data point in the figure represents the ROC area of the predictive algorithm calculated using a 1 hour block of time, taken at different time points relative to the event. Thus, the point t=0 hours represents the performance of the algorithm with data obtained between zero and one hour prior to deterioration. By design, the algorithm has the highest performance approximately one to two hours prior to deterioration (ROC Area=0.91). As the forecasting time was increased, the performance of the algorithm was observed to decrease. Approximately four to five hours prior to a deterioration event, the ROC area was found to be close to 0.5, indicating that the algorithm could no longer discriminate between pre-deterioration data and non-deterioration measurements.

The distribution of all measurements of the RRI generated by the model is not Gaussian, as it is constructed in one embodiment as an odds ratio which is bounded at zero with a median at 1. The most common observed value was 0.6. RRI values greater than or equal to 3.3 are observed only 10% of the time, while values of RRI greater than or equal to 10 are observed only 2% of the time in this population. If this risk exposure were evenly distributed in the cohort, then every subject would spend approximately 30 minutes a day with an RRI greater than 10. However, it is reasonable to hypothesize that subjects with greater severity of illness have more exposure to pre-deterioration physiology, whether or not an actual event occurs. Further, it is a logical hypothesis that subjects who deteriorated also experienced a higher burden of pre-deterioration physiology exposure.

Therefore a classification model such as described above can discriminate a state of pre-deterioration from a state of stability on subjects with parallel circulatory anatomy and mixing physiology. Standard monitoring for these patients has a limited ability to discriminate between these states due to abnormalities of baseline vital signs when compared with patients who have normal serial circulation. The intent of real time classification of patient physiology is to provide a rapid detection of impending clinical deterioration giving providers increased time to assess and intervene.

Several studies have been published describing different predictive risk scores for different clinical events and populations. One study has shown that cardiac arrest events could be anticipated in adult population in the setting of a cardiac ward using vital sign data. Another study developed and measured the performance of the bedside-pediatrc early warning system (PEWS) score for determining the need for up-transfer to an intensive care unit (ICU) for hospitalized pediatric patients. Another study described the performance of an algorithm to estimate the likelihood of arrest in children with heart disease using data from a physical exam for daily care management. There are also several published categorical risk metrics for children which can be evaluated at the time of ICU admission, for example, the Pediatric Risk of Mortality (PRISM) and Pediatric Index of Mortality (PIM) scoring systems. These studies have several common features. Each study used a logistic regression model with a combination of vital signs and physical exam results to estimate risk. Data was manually collected by staff at intervals which were typically several hours long. Each study focused on estimating the risk of deterioration in the next 24-48 hours to assess the need for changes in daily management of care. However, none of these studies have addressed the need to improve the real time detection of precursors to deterioration in order to improve the clinical response when events do occur. To our knowledge, no study to date has focused on detecting precursors to deterioration in children with congenital heart disease and parallel circulations for both ICU and non-ICU admissions.

The RRI has several advantages over traditional risk scores. For example, because the RRI is derived from continuous physiologic data, the RRI may be updated automatically, continuously, and in real time without impacting existing clinical workflow. Since the RRI was derived using all of the physiologic data generated by the infant during their hospitalization, the metric is applicable in both ICU and non-ICU environments. Furthermore, the inputs to the model in one embodiment are calibrated to an individual subject, relative to a baseline value for each individual (Equation 2). This is important since the baseline physiologic parameters can vary widely between subjects, and for this complex population there is little consensus as to what constitutes 'normal' or even 'acceptable' for a given physiologic parameter.

The RRI provides a highly sophisticated decision support tool to clinicians. The physiologic inputs into the index were selected to be sensitive to different mechanisms of patient decomposition. Therefore, while an increase in the RRI will not indicate a priori what type of clinical intervention may be required, the index signals the need for additional medical surveillance and possibly additional diagnostic investigations, such as an echocardiogram or arterial blood sampling. The pre-clinical detection of impending deterioration allows time for a thorough assessment to be performed, so that any necessary interventions could be applied proactively. For example, if it is shown to be robust in larger groups of patients, an increase in the index may be an indication for priming an extracorporeal membrane oxygenation (ECMO) circuit or mobilizing the ECMO team, so that valuable time can be saved, in the event of serious deterioration. Furthermore, restoration of the index to baseline levels is likely to be an indication of successful therapeutic and resuscitative measures.

Figure 8:
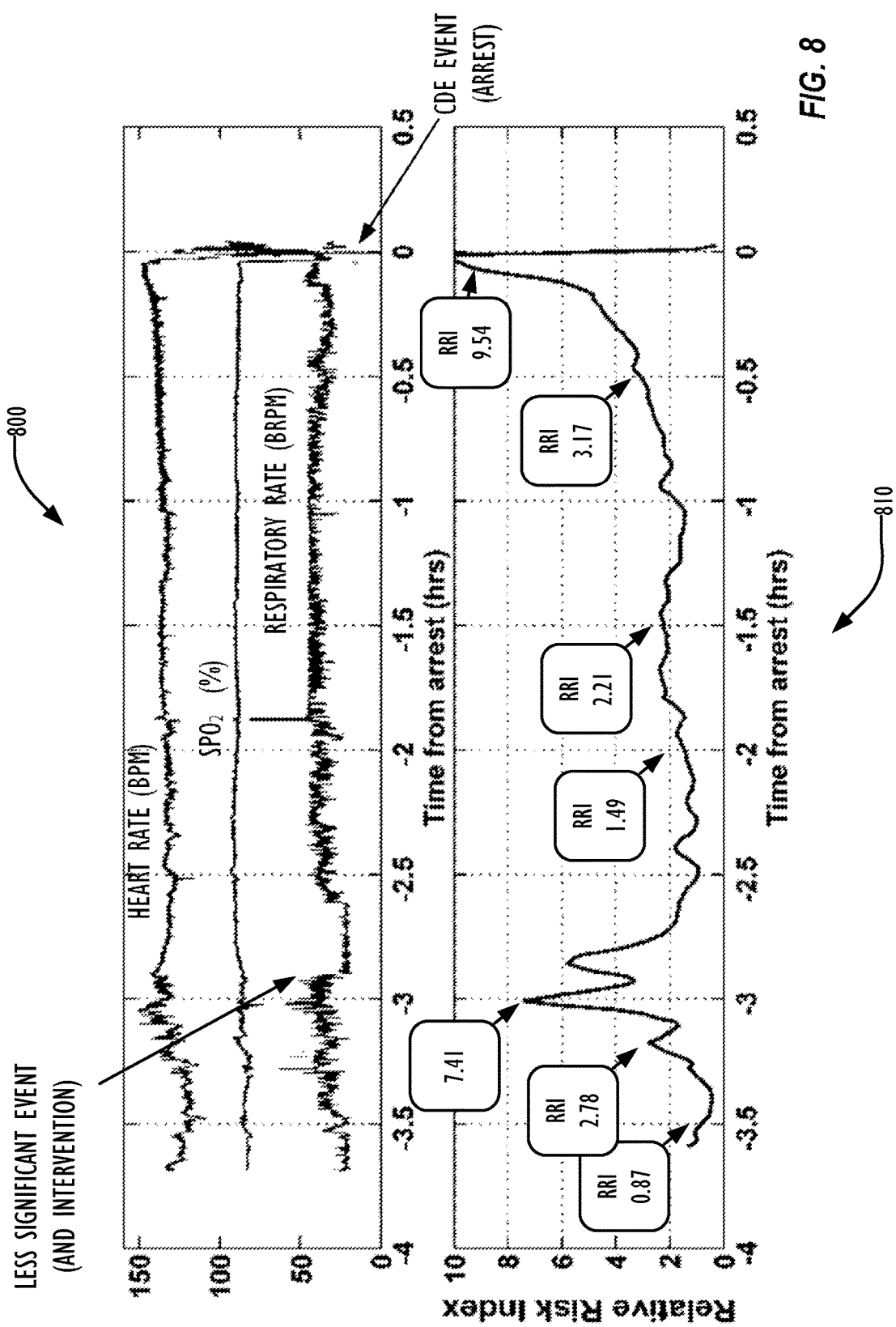
FIG. 8 is a pair of graphs comparing vital signs for a patient and a clinical metric generated by a predictive model according to one embodiment.
Figure 9:
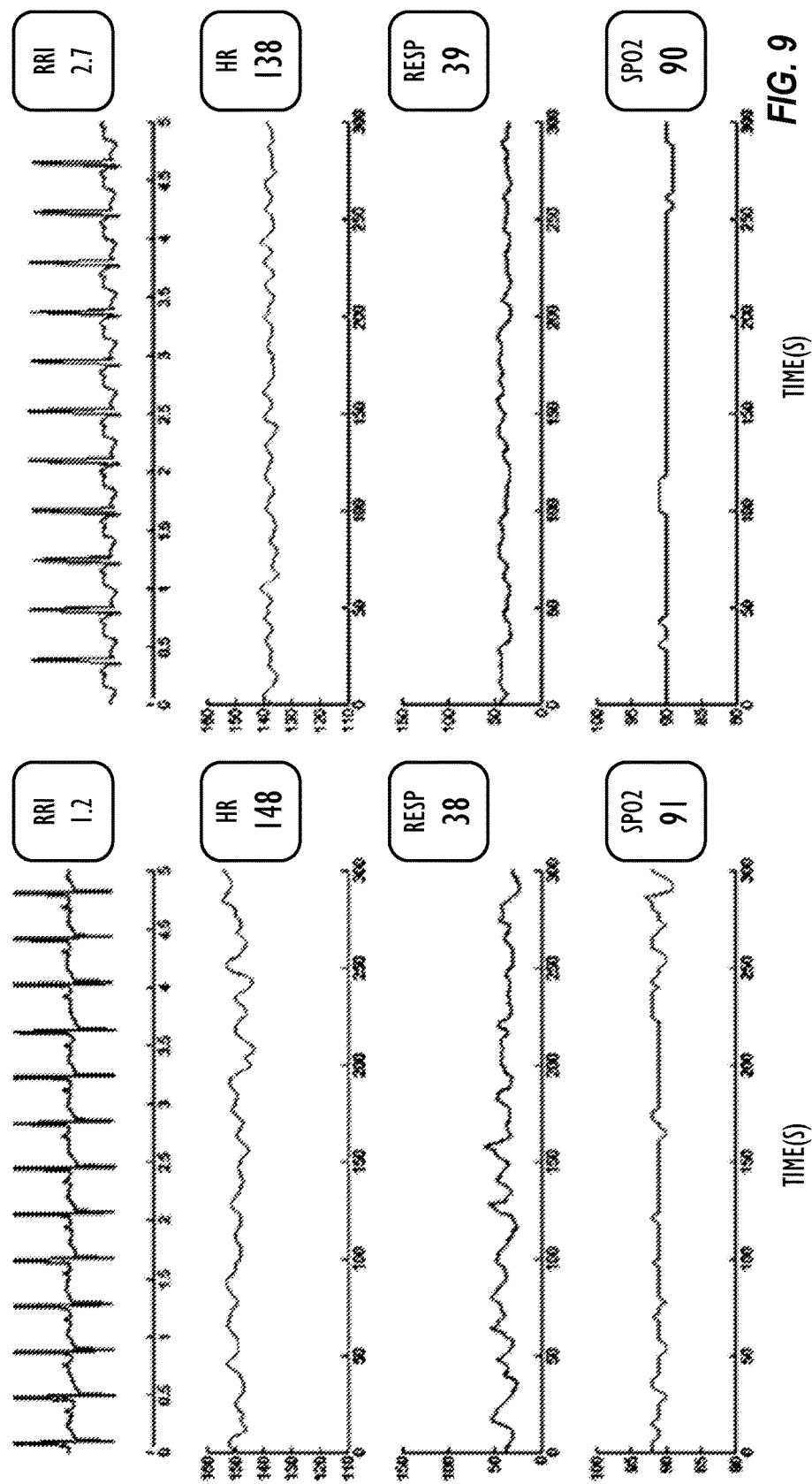
FIG. 9 is the graphs of FIG. 2 with the addition of a display of a clinical metric according to one embodiment.

The RRI provides a calibrated means of comparing changes in the likelihood of an event over time. As an example, the graph 800 of FIG. 8 depicts the vital sign data of a patient just prior to an arrest, which in this graph occurs at t=0. A second unidentified sub-event occurs around three hours previously, at t−3. The lower graph 810 illustrates the RRI calculated for this period of time according to one embodiment. Two hours before the primary event, the risk index is calculated to be 1.49. 1.5 hours before the primary event, the risk index increases to 2.21. This indicates that the patient is now exhibiting physiological signs which are associated with a 2.2 fold increased likelihood of an arrest within the next 1-2 hours. One hour before the event, the risk index increases to a value of 2.33. 30 minutes before the event, the risk index continues to increase to 3.17. And over the next 20 minutes, the risk index dramatically increases to 9.5. 8 minutes later, the patient arrests. The RRI displays the same characteristics in an earlier unidentified event, rising from a value of 0.87 to 2.78 to 7.41 just prior to the time at which physicians intervened. Around this time, in this example the clinical staff reduced the infusion rate of epinephrine by 20% and started Fentanyl, Midazolam, and Morphine. The relative risk index subsequently fell to average levels before rising again in anticipation of the eventual arrest.

Thus, the continuous reporting of the RRI shows a pattern of progressive decompensation from which two things can be clearly concluded: First, the physiology analyzed in this patient showed a pattern that was distinct from a cohort with similar physiology, and second that this pattern is significantly associated with pre-deterioration physiology in the same cohort.

Therefore, providing the RRI clinical metric to a clinical staff continuously and in real time provides them with a more objective means of assessing the risk of arrest in the near future for patients after stage 1 palliation surgery. Applying this metric to our previous monitor illustrated in FIG. 2, using the RRI a clinician may easily distinguish that the patient on the right is at a lower risk of arrest in the next hour then the patient on the left.

Figure 10:
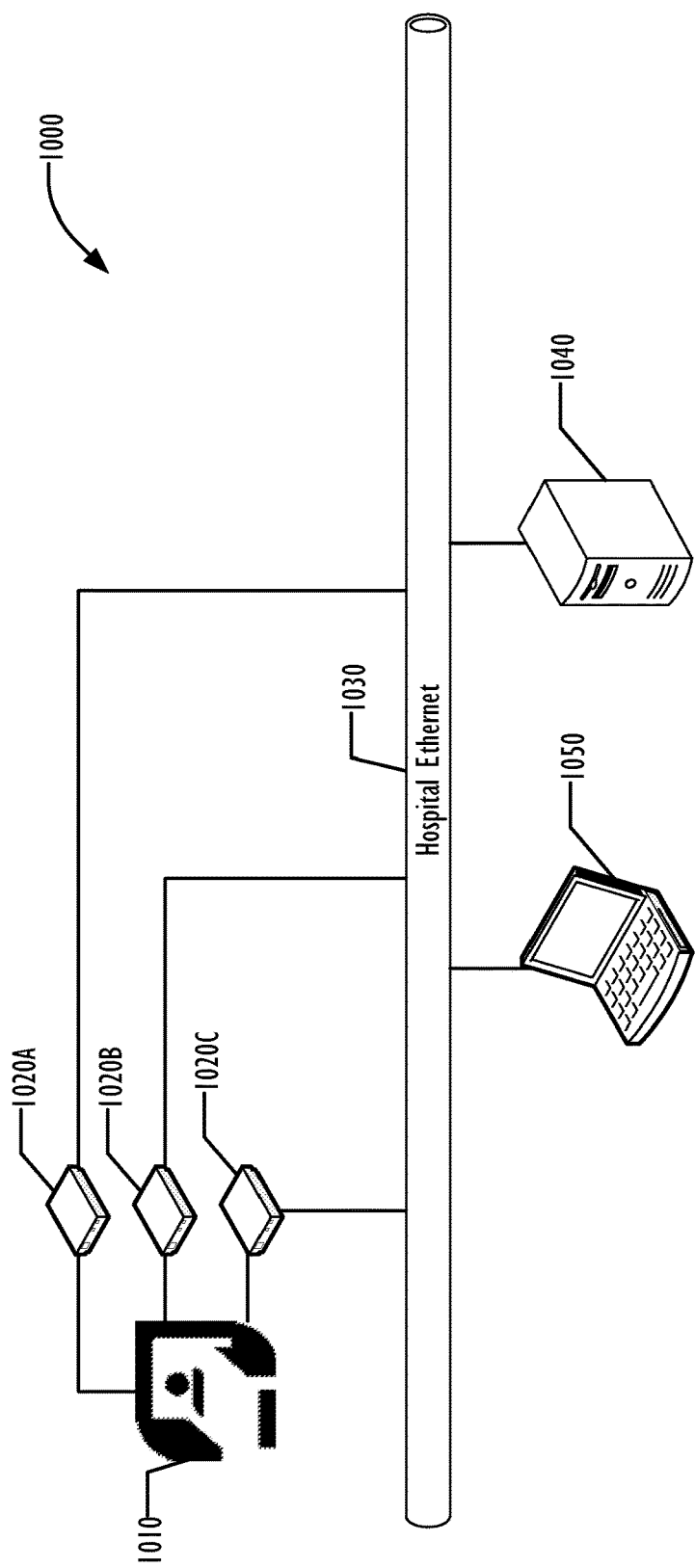
FIG. 10 is a block diagram of a system for generating and displaying a clinical metric according to one embodiment.

FIG. 10 is a block diagram that illustrates a system 1000 in which the clinical metric techniques may be deployed. A patient 1010, such as an infant in an ICU is connected to a plurality of physiological sensors 1020A-C, which may be any desired type of sensor. These sensors 1020A-C may then be connected, directly or through intermediary devices, to a hospital network such as the hospital Ethernet 1030 illustrated in FIG. 10. Any type of data connection, wired or wireless, may be used. In one embodiment, a server 1040 collects the patient physiological data continuously in real time, and calculates a real time RRI value. The RRI value may then be transmitted to a clinical display such as the laptop 1050. In one embodiment, if the RRI value exceeds a predetermined RRI threshold, an alarm may be automatically generated using any desired hospital alarm system. Any desired predetermined relationship with the threshold may be used. For example, in one embodiment an alarm may be generated if the RRI value meets the threshold. In another embodiment, the RRI value may be a decreasing value, such that a lower RRI value indicates a higher risk of sudden onset of deterioration. In such an embodiment, the alarm may be triggered by the RRI value reaching (or falling below) the threshold value. The elements illustrated in FIG. 10 are illustrative and by way of example only. Other devices, and connections between the devices may be used. In some embodiments, the server 1040 may provide storage for the physiological data and the calculated RRI value for historical, quality, or clinical research studies or any other desired purpose, for example. Although shown as a single network, any number of interconnected networks may be employed for the system 1000, and any number of the indicated devices may be deployed. Although illustrated for a single patient for clarity, implementations may deploy the elements of the system 1000 for all or any desired portion of the beds of the implementing facility. Some of the elements of the system 1000 may be remote from the clinical facility where the patients are monitored. Software for performing the techniques described herein may be stored as instructions on a computer readable medium; when executed the instructions cause the server 1040 to perform the actions. The computer readable medium may be any non-transitory type of medium, including, without limitation, memory circuitry, optical media, magnetic media, etc. The server 1040 may be any type of programmable device capable of performing the actions described here, whether or not called a server.

Although generally described herein as deployed in a clinical setting such as in an intensive care unit of a hospital, the system and techniques described may be implemented in other settings, including home monitoring settings. In a home monitoring setting, home measuring devices, measuring the same things as intensive care unit monitoring devices, are deployed and connected to a network for delivery of the data to the server 1040.

Figure 11:
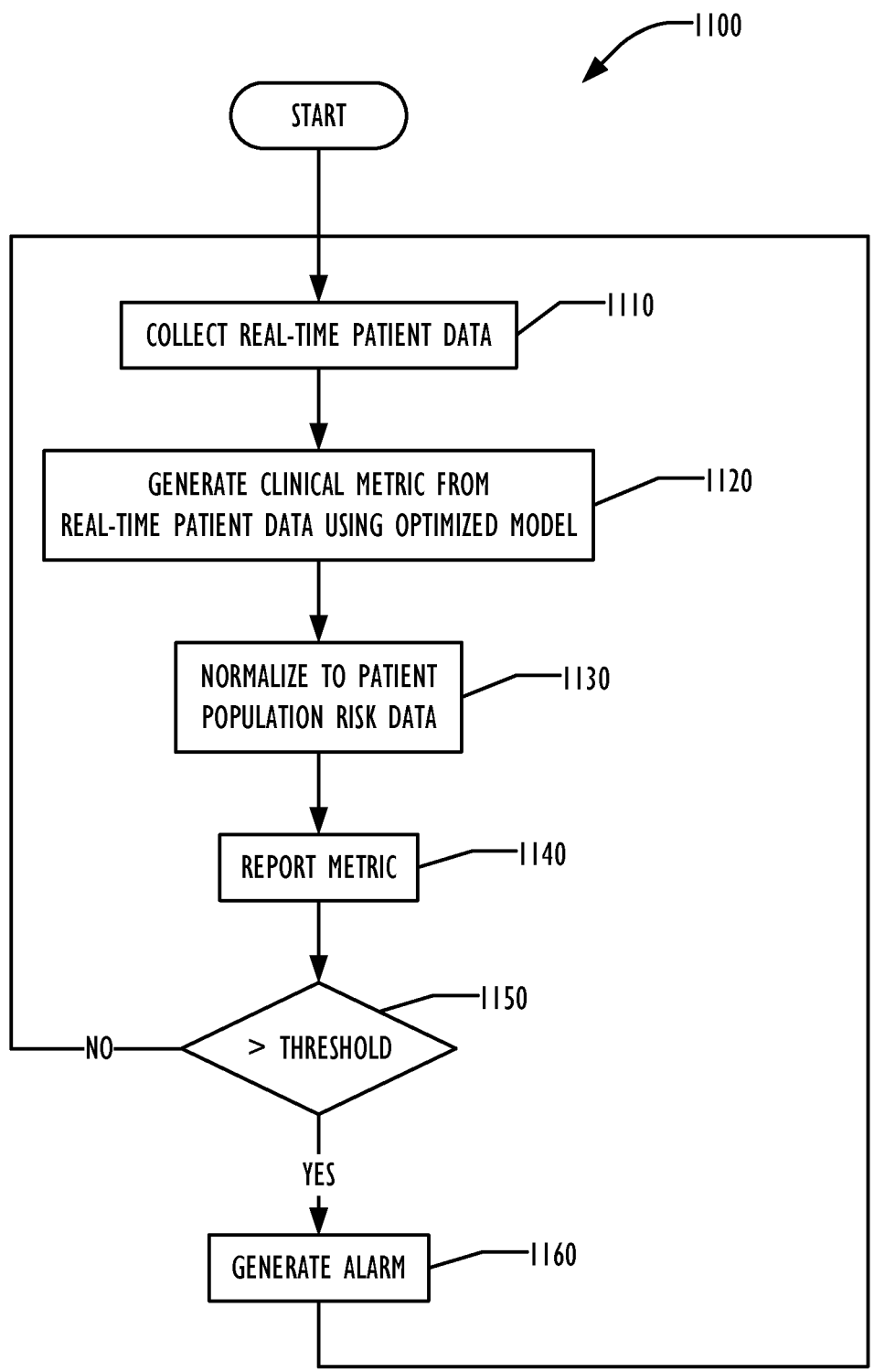
FIG. 11 is a flowchart illustrating a technique for generating a clinical metric according to one embodiment.

FIG. 11 is a flowchart illustrating a technique 1100 for generating a clinical metric according to one embodiment. In block 1110, real time patient physiological data is collected continuously by a patient data monitoring system from a plurality of patient physiological sensors, typically attached to the patent. Any type of physiological sensor may be used, generating any type of waveform or data indicating the physiological condition corresponding to the sensor. A sensor may in some situations generate more than one type of physiological data. The sensor data is transmitted across one or more networks to a collecting computer, possibly through intermediary devices and networks. The collecting computer may store the collected real time physiological data in any desired way.

In block 1120, a clinical metric, such as the RRI described above, is generated from the real time patient physiological data using an optimized model such as the one described above. The clinical metric provides predictive information about the risk of the onset of cardiorespiratory deterioration of the corresponding patient that would cause a rapid response event.

In block 1130, the clinical metric may be normalized to patient population risk data, as described above. Preferably, the clinical metric may also be adjusted based on a patient-specific baseline data, using previously collected patient physiological data. In one embodiment, the previously collected patient physiological data is data collected 6 hours prior to the current collection time. The 6 hour time period is illustrative and by way of example only, and any desired predetermined time period prior to the current collection time may be used.

In block 1140, the clinical metric may be displayed, typically on a monitor screen of a clinical monitoring system that also displays patient physiological data, which may or may not be the same patient physiological data that is used to generate the clinical metric. The display of the clinical metric may be performed in any desired way, including numerical, graphical, or textual displays. In a non-clinical setting, such as a home monitoring system, the clinical metric may be displayed on a home monitor, in addition to or instead of a clinical monitoring system.

In block 1150, the clinical metric may be compared to a predetermined threshold value. Embodiments may be configured to determine whether the clinical metric meets, exceeds, or has any other relationship to the predetermined threshold value. If the comparison indicates the configured relationship exists, such as the clinical metric exceeds the threshold value, then in block 1160 an alarm may be generated in a clinical alarm system, to alert clinical staff that a deterioration event is predicted. The alarm thus allows clinical staff to take medically indicated actions that may prevent or reduce the effects of the predicted event.

The actions of blocks 110-1160 may be performed continuously as long as the patient is in the facility and is considered at risk, which may be the entire time the patient is in the facility. Although indicated as sequential actions in the flowchart, the actions indicated by the various blocks may be performed asynchronously in one embodiment, for example allowing the patient data collection of block 1110 to be performed continuously while the clinical metric is being generated and displayed and alarms possibly generated. The order of the actions illustrated in the flowchart may also be performed in alternate order or simultaneously, as desired. For example, instead of generating the alarm after displaying the RRI, embodiments may generate the alarm prior to or at the same time as displaying the RRI value. An embodiment may choose to omit the display of the clinical metric except when the clinical metric has the configured relationship with the threshold, so that the metric is only displayed when an alarm would be generated.

Although described above as collected continuously, certain kinds of physiological data, such as a pulse rate, by their nature may be repeatedly collected at intervals, but such repeated collection is considered herein to be a continuous collection of the data.

While certain exemplary embodiments have been described in details and shown in the accompanying drawings, it is to be understood that such embodiments are merely illustrative of and not devised without departing from the basic scope thereof, which is determined by the claims that follow.

We claim:

1. A method of predicting an onset of cardiorespiratory deterioration of a patient, comprising:
   collecting real time patient physiological data from a plurality of patient physiological sensors;
   generating a clinical metric associated with a likelihood of cardiorespiratory deterioration of the patient in a predetermined future time period in real time, based on the real time patient physiological data; and
   generating an alarm if the clinical metric has a predetermined relationship with a threshold value,
   wherein the patient is an infant after Stage 1 surgical palliation for hypoplastic left heart syndrome.

2. The method of claim 1, wherein the predetermined relationship is greater than or equal.

3. The method of claim 1, wherein generating a clinical metric comprises:
   generating the clinical metric based on the real time patient physiological data and a patient-specific baseline physiological data.

4. The method of claim 3, wherein generating the clinical metric comprises:
   normalizing the clinical metric to an average risk of deterioration in a patient population; and
   calculating a risk index value in real time based on the real time patient physiological data and the patient-specific baseline physiological data.

5. The method of claim 1, further comprising:
   reporting the clinical metric in real time.

6. The method of claim 1, wherein the predetermined future time period is one to two hours in the future.

7. The method of claim 1, wherein generating a clinical metric comprises:
   optimizing a model based upon one or more of:
      heart rate;
      respiration rate variability;
      $SpO_2$,
      3D ST segment variability;
      ST segment; and
      heart rate variability.

8. The method of claim 1, further comprising:
   collecting a patient-specific baseline data from the patient physiological sensors, and
   wherein generating a clinical metric comprises:
      generating the clinical metric at time t based upon real time patient physiological data collected at time t and patient-specific baseline data collected at a predetermined time before time t.

9. The method of claim 1, wherein the clinical metric is a clinical metric associated with a likelihood of cardiac arrest in an infant after Stage 1 surgical palliation.

10. The method of claim 1, wherein generating a clinical metric comprises:
    optimizing a model using logistic regression; and
    employing the model to analyze the real time patient physiological data.

11. The method of claim 1, wherein the cardiorespiratory deterioration comprises one or more of:
    an intubation event;
    a shock;
    a respiratory arrest;
    a cardiac arrest; and
    hypoxemia.

12. A non-transitory computer readable medium, on which are stored instructions, comprising instructions that when executed cause a patient data monitoring system to:
    collect real time patient physiological data from a plurality of patient physiological sensors associated with a patient, wherein the patient is an infant after Stage 1 surgical palliation for hypoplastic left heart syndrome;
    generate a real time clinical metric associated with a likelihood of cardiorespiratory deterioration of the patient within a predetermined future time period, based on the real time patient physiological data; and
    generate an alarm if the clinical metric has a predetermined relationship with a predetermined threshold value.

13. The computer readable medium of claim 12, wherein the instructions that when executed cause the patient data monitoring system to generate an alarm comprise instructions that when executed cause the patient data monitoring system to generate the alarm if the clinical metric exceeds the predetermined threshold value.

14. The computer readable medium of claim 12, wherein the instructions that when executed cause the patient data monitoring system to generate a real time clinical metric comprise instructions that when executed cause the patient data monitoring system to:
    generate the clinical metric based on real time patient physiological data and a patient-specific baseline physiological data.

15. The computer readable medium of claim 14, wherein the patient-specific baseline physiological data comprises real time patient physiological data collected from the plurality of patient physiological sensors at a predetermined prior time period.

16. The computer readable medium of claim 12, wherein the instructions that when executed cause the patient data monitoring system to generate a real time clinical metric comprise instructions that when executed cause the patient data monitoring system to:
    normalize the clinical metric to an average risk of cardiorespiratory deterioration in a patient population.

17. The computer readable medium of claim 12, wherein the instructions that when executed cause the patient data monitoring system to generate a real time clinical metric comprise instructions that when executed cause the patient data monitoring system to:
    analyze the real time patient physiological data using a model optimized by logistic regression of patient population data.

18. The computer readable medium of claim 17,
    wherein the patient population comprises a population of hypoplastic left heart syndrome post-surgical palliation single ventricle infants, and
    wherein the model is based on one or more of:
       heart rate;
       respiration rate variability;
       $SpO_2$,
       3D ST segment variability;
       ST segment; and
       heart rate variability.

19. The computer readable medium of claim 12, wherein the cardiorespiratory deterioration comprises one or more of:
    an intubation event;
    a shock;
    a respiratory arrest;
    a cardiac arrest; and
    hypoxemia.

20. The computer readable medium of claim 12, wherein the predetermined future time period is one to two hours in the future.

* * * * *